United States Patent [19]

Harman

[11] 3,988,582
[45] Oct. 26, 1976

[54] BLOWN FILM THICKNESS GAUGE

[75] Inventor: Randall W. Harman, San Juan Capistrano, Calif.

[73] Assignee: Nucleonic Data Systems, Inc., Irvine, Calif.

[22] Filed: Aug. 28, 1975

[21] Appl. No.: 608,519

[52] U.S. Cl. ............................. 250/272; 250/273; 425/72 R; 425/141
[51] Int. Cl.² ....................................... G01N 23/20
[58] Field of Search .......... 250/272, 273, 274, 277, 250/278, 279; 425/72, 141

[56] References Cited
UNITED STATES PATENTS

| | | | |
|---|---|---|---|
| 2,711,480 | 6/1955 | Friedman | 250/272 X |
| 3,122,784 | 3/1964 | Solliffe | 425/141 |
| 3,714,309 | 1/1973 | Biglano | 425/72 X |
| 3,767,920 | 10/1973 | Kido et al. | 250/277 X |

Primary Examiner—Davis L. Willis
Attorney, Agent, or Firm—Harris, Kern, Wallen & Tinsley

[57] ABSTRACT

Apparatus for measuring the thickness of the plastic film of a blown film machine, making the measurement adjacent the extruder die without contacting the film. A radiation source and detector spaced from one side of the plastic film and a metal member spaced from the other side, with the detector receiving fluorescent x-rays from the metal member produced by source photons and receiving back scattered source photons from the film and the metal member, with both the fluorescent x-rays and the scattered photons producing indications of thickness.

18 Claims, 3 Drawing Figures

BLOWN FILM THICKNESS GAUGE

BACKGROUND OF THE INVENTION

This invention relates to measuring thickness of sheet material without contacting the material and is particularly directed to measuring material thickness in a blown film sheet and bag machine.

Plastic sheet and bags are often manufactured in blown film machines. A typical blown film machine has a base with a source of heated plastic and an air supply. The plastic is extruded upward through an annular die in a cylindrical configuration. Air is blown into the interior of the cylinder expanding the plastic to the desired size. The upwardly moving plastic sleeve or bubble freezes or hardens a short distance above the die and is lifted and flattened or collapsed by a mechanism at the upper end of the bubble producing a flattened double layer sleeve for subsequent operation. A typical machine can produce plastic in thicknesses up to 50 to 100 mils with bubbles in the order of 12 feet tall and 2 to 8 feet in diameter.

The air blown into the interior of the bubble is heated, and the thickness of the sheet is controlled by controlling the air temperature and the air pressure. It is preferred to have the extruder rotate slowly, typically one revolution per minute, for improved uniformity of thickness.

Two configurations for measuring thickness are presently being used. One system utilizes a beta radiation source which rests against the plastic sleeve directing beta rays through the sleeve and measuring the scattered radiation from the air on the other side of the sleeve. The beta source must maintain continuous contact with the sleeve and produces a dimple in the bubble. There are a number of disadvantages of this system. The measurement is a function of the air density and air temperature which introduces considerable error. The measurement must be made by contact with the solid plastic above the frost line and it is difficult to relate the measured location to a location on the extruder die. This is significant since the thickness varies around the circumference of the die and it is desirable for the operator to know the exact location on the annular die which needs adjusting. Also, the contact of the source with the material produces distortion and friction problems.

In the second system, thickness is measured at the flattened double layer either by direct contact or by the beta gauge previously described. The major problem with this type of measurement resides in the fact that the measurement is made too far from the extruder die prohibiting close control of film thickness.

It is an object of the present invention to provide a new and improved apparatus and method for measuring sheet thickness of a blown film machine. A particular object is to provide for measurement without contact with the sheet material and to provide measurement immediately adjacent the extruder die. It is a further object of the invention to provide a new and improved method and apparatus for measurement of thickness suitable for use with various sheet type materials which are capable of being penetrated by x-rays, such as plastics, rubbers, gums and metals.

SUMMARY OF THE INVENTION

A typical blown film machine has a plastic extruder with a die for extruding an elongate plastic bubble, an air system for supplying air under pressure to the interior of the bubble, and a collector for receiving the bubble. The thickness gauge includes a metal member which serves as a target and is positioned adjacent the extruder die within and spaced from the bubble, and an x-ray photon source and a radiation detector mounted outside and spaced from the bubble for directing x-ray photons from the source through the film to the target member and for receiving source photons scattered from the bubble and from the target member and receiving fluorescent x-rays from the target member. Two measurements for thickness can be made, with the intensity of the scattered source photons varying as a function of film thickness and with the intensity of the fluorescent x-rays varying as a function of film thickness. Typically a pulse height analyzer is utilized to measure the radiation intensity in counts in the energy band of the x-ray source and in the energy band of the fluorescent x-rays, with the analyzer output being calibrated in film thickness for driving an indicator such as a meter or digital readout or the like.

DESCRIPTION OF THE PREFERRED EMBODIMENT

Figure 1:
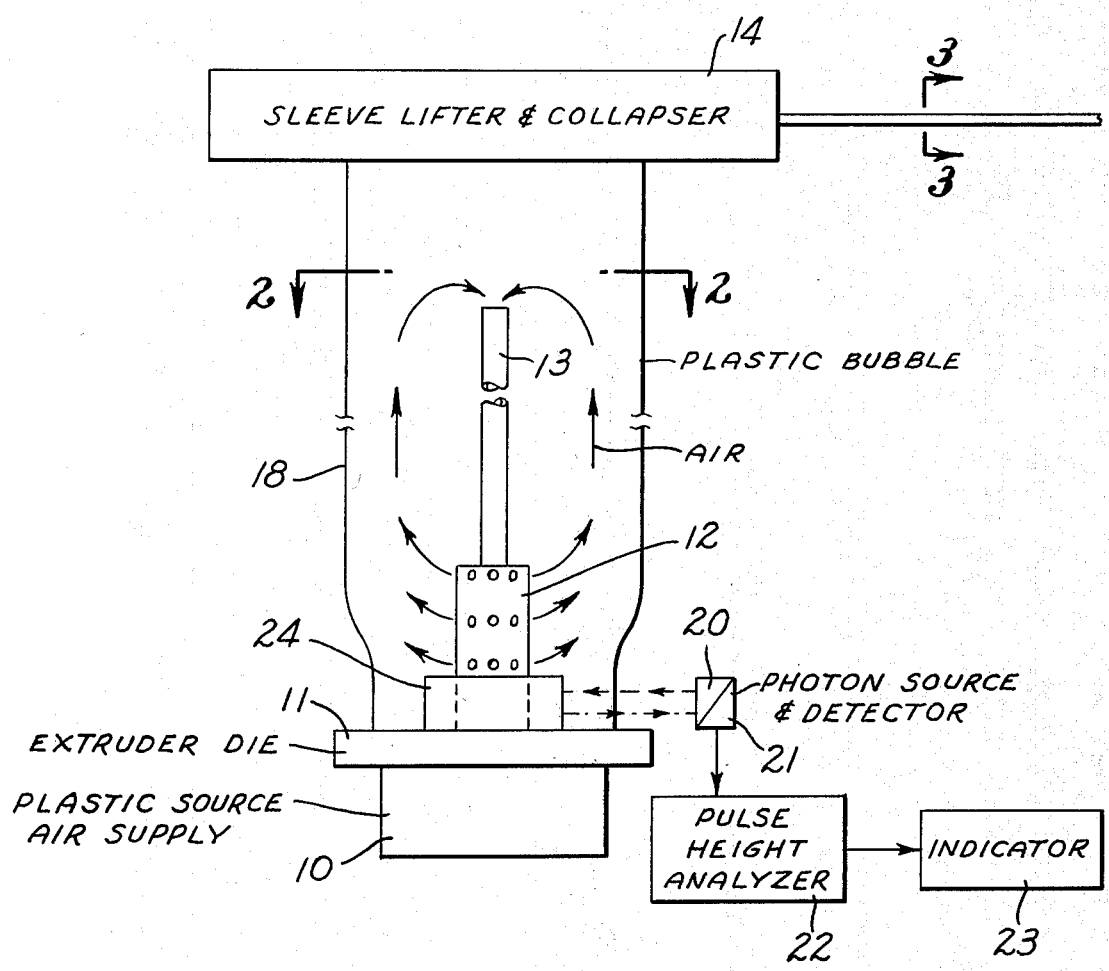
FIG. 1 is a side view of a conventional blown film machine with a thickness gauge incorporating the presently preferred embodiment of the invention.
Figure 2:
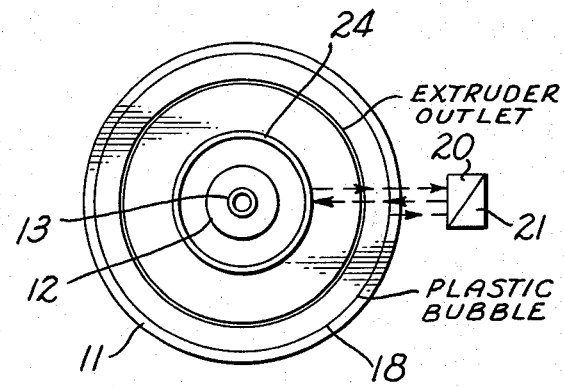
FIG. 2 is a sectional view taken along the line 2—2 of FIG. 1.
Figure 3:
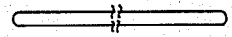
FIG. 3 is a sectional view taken along the line 3—3 of FIG. 1.

A conventional blown film machine is illustrated in FIG. 1 having a base 10 providing the source of plastic and the air supply, with an extruder die 11 carried on the base 10. An air outlet 12 projects upward from the base above the die, with an inlet 13 positioned above the outlet 12. A sleeve lifter and collapser 14 is positioned above the base 10. In operation, the heated plastic is forced upward through the extruder die forming a sleeve or bubble 18. Heated air is expelled from the air outlet 12 under the control of the operator to expand the sleeve to the desired size. The blown film machine is a continuously operating machine, with the plastic material solidifying or freezing a distance about a foot above the extruder die and further cooling as it moves upward to the lifter. The air pressure within the bubble maintains the bubble in a upright position and the lifter provides a lifting force for raising the bubble. The lifter includes a plurality of rollers which collapse the sleeve into a flat tube and move it away from the blown film machine for further operations and/or cutting and stacking or rolling.

Typically, the extruder die rotates slowly such as in the order of one revolution per minute, and the operator controls the size of the bubble and the thickness of the material by adjusting the plastic temperature, the die size, the air temperature and the air pressure. The air patterns within the bubble are generally indicated by the arrows, with air flowing out the openings of the outlet 12 and returning through the stack 13. Blown film machines are on the market and in use and need not be described further herein. Reference may be made to the standard machines for further details of construction and operation.

The thickness gauge of the present invention includes an x-ray photon source 20 and a radiation detector 21 mounted in a single housing adjacent but spaced from the plastic bubble, a pulse height analyzer 22, and an indicator 23. Conventional components may be chosen for these elements of the system. A metal member 24 is mounted on the base inside the bubble adjacent the extruder die. In the preferred embodiment, the member 24 is an annulus in the order of a few inches high and serves as a target for the x-ray photon source as the member 24 rotates with the extruder die. Alternatively, a stationary metal member could be utilized, typically in the shape of a disc a few inches in diameter. In another alternative, the air outlet 12 can serve as the metal member.

In operation, x-ray photons from the source 20 are directed through the sheet material 18 to the member 24. These source photons are scattered by the sheet material and are scattered by the metal member. Also, the incident source photons at the metal member produce fluorescent x-rays from the metal member. The radiation detector 21 receives the scattered source photons and the fluorescent x-rays. The pulse height analyzer 22 or other appropriate circuitry may be set to provide an output varying as a function of the intensity of the scattered photons or the intensity of the fluorescent x-rays or two outputs, one varying as a function of the scattered photons and one varying as a function of the fluorescent x-rays. Typically the pulse height analyzer will have two pass bands, one designed to pass detector outputs in the energy band of the photon source and one to pass detector outputs in the energy band of the fluorescent x-rays of the metal member 24. The detected radiation is counted over a period of time for each of the energy bands providing outputs in terms of count rate which are readily calibrated in terms of film thickness. The count rate for scattered source photons varies as a direct function of film thickness while the count rate for fluorescent x-rays varies as an inverse function of film thickness.

While the system as described can utilize both the scattered source photon and fluorescent x-ray modes, the fluorescent x-ray mode is preferred for thinner films and the scattered source photon mode is preferred for thicker films because of better sensitivities. For the fluorescent x-ray mode, the source photon energy should be greater than that required to produce fluorescent x-rays from the target member. Typically Americium 241 can be used as the source with the member 24 formed of iron. The metal member 24 should be sufficiently thick to produce the maximum number of iron x-rays and desirably should be at least 0.015 inches thick.

As indicated previously, source photons are scattered by the plastic film as well as by the member 24, with the thicker film providing more scattering at the film.

While the terms thinner and thicker have been utilized in the preceding discussion, in radiation measurement the mass per unit area of the sheet material is more meaningful. A thicker material would be one where the mass per unit area is greater than 100 to 200 milligrams per square centimeter, while a thinner material would be one where the mass per unit area is less than 100 to 200 milligrams per square centimeter.

The thickness measuring system of the present invention requires no contact with the material being measured. In the blown film machine, the plastic bubble can move in and out and can rotate without any effect on the measurement equipment. Measurement may be made at any location along the bubble and in particular, can be made below the frost line where the plastic freezes or solidifies, which occurs about 12 inches from the outlet of the extruder die. The ability to make the measurement directly adjacent the extruder die provides the operator with a direct indication of the thickness of the material at a particular location along the periphery of the die while the die is rotating.

While the measuring system is described herein as applied to a blown film machine for measuring the thickness of a plastic bubble, the system is also suitable for measuring thickness of other sheet materials which are capable of being penetrated by x-rays, such as sheet plastics, rubber, gums and metals.

I claim:
1. In a thickness gauge for a blown film machine having a plastic extruder with a die for extruding an elongate plastic bubble, an air system for supplying air under pressure to the interior of the bubble, and a bubble collector receiving the bubble, the combination of:
   a metal member;
   means for mounting said member adjacent said die and within and spaced from said bubble;
   a source of x-ray photons;
   a radiation detector; and
   means for mounting said source and detector outside and spaced from said film for directing photons from said source through said film to said member and receiving photons from said member, with the radiation intensity at said detector being a function of the thickness of said film.

2. A thickness gauge as defined in claim 1 wherein said die is circular and said metal member is an annulus coaxial with said die.

3. A thickness gauge as defined in claim 1 wherein said extruder die rotates relative to said source and detector.

4. A thickness gauge as defined in claim 1 wherein said detector includes means providing an output varying as a function of intensity of source photons scattered by said film and said metal member.

5. A thickness gauge as defined in claim 1 wherein said detector includes means providing an output varying as a function of intensity of fluorescent x-rays of said metal member produced by source photons.

6. A thickness gauge as defined in claim 1 wherein said detector includes means providing a first output varying as a function of intensity of source photons scattered by said film and said metal member and a second output varying as a function of intensity of fluorescent x-rays of said metal member produced by source photons.

7. A thickness gauge as defined in claim 1 wherein said metal member is a portion of said air system.

8. A thickness gauge as defined in claim 1 including a thickness indicator having the detector output as an input and providing an output indication of thickness of the blown film.

9. A thickness gauge as defined in claim 1 wherein said source is Americium 241 and said metal member is iron.

10. A thickness gauge as defined in claim 1 wherein said source, detector and metal member are positioned between said die and the frost line of said bubble.

11. A thickness gauge as defined in claim 1 wherein said source, detector and metal member are spaced not more than a few inches from said die as measured along the axis of the bubble.

12. In a thickness gauge for a single layer sheet of material, the combination of:
   a metal member;
   a source of x-ray photons;
   a radiation detector; and
   means for mounting said source and detector on one side of and spaced from the sheet, and said metal member on the opposite side of and spaced from the sheet, for directing photons from said source through said sheet to said member and receiving photons from said member, with the radiation intensity at said detector being a function of the thickness of said sheet.

13. A thickness gauge as defined in claim 12 wherein said detector includes means providing an output varying as a function of intensity of source photons scattered by said sheet and said metal member.

14. A thickness gauge as defined in claim 12 wherein said detector includes means providing an output varying as a function of intensity of fluorescent x-rays of said metal member produced by source photons.

15. A thickness gauge as defined in claim 12 wherein said detector includes means providing a first output varying as a function of intensity of source photons scattered by said film and said metal member and a second output varying as a function of intensity of fluorescent x-rays of said metal member produced by source photons.

16. A method of measuring the thickness of single layer sheet material without contacting the material, including the steps of:
   directing x-ray photons from a source through the sheet material to a target with the source and target spaced from the sheet material:
   detecting at a location on the same side of the sheet material as the source, source photons scattered from the sheet material and from the target; and
   indicating the thickness of the sheet material as a function of the detected radiation counts in the energy band of the source.

17. A method of measuring the thickness of single layer sheet material without contacting the material, including the steps of:
   directing x-ray photons from a source through the sheet material to a target spaced from the sheet material;
   detecting at a location on the same side of the sheet material as the source, fluorescent x-rays generated at the target by incident x-ray photons; and
   indicating the thickness of the sheet material as a function of the detected radiation counts in the energy band of the target fluorescent x-rays.

18. The method as defined in claim 17 including the steps of:
   detecting at a location on the same side of the sheet material as the source, source photons scattered from the sheet material and from the target; and
   indicating the thickness of the sheet material as a function of the detected radiation counts in the energy band of the source.

* * * * *